(12) United States Patent
Adachi et al.

(10) Patent No.: US 8,521,271 B2
(45) Date of Patent: Aug. 27, 2013

(54) BRAIN WAVE IDENTIFICATION METHOD ADJUSTING DEVICE AND METHOD

(75) Inventors: Shinobu Adachi, Osaka (JP); Koji Morikawa, Kyoto (JP)

(73) Assignee: Panasonic Corporation, Osaka (JP)

( * ) Notice: Subject to any disclaimer, the term of this patent is extended or adjusted under 35 U.S.C. 154(b) by 1193 days.

(21) Appl. No.: 12/439,178

(22) PCT Filed: Oct. 4, 2007

(86) PCT No.: PCT/JP2007/069451
§ 371 (c)(1),
(2), (4) Date: Feb. 27, 2009

(87) PCT Pub. No.: WO2008/056492
PCT Pub. Date: May 15, 2008

(65) Prior Publication Data
US 2010/0004556 A1  Jan. 7, 2010

(30) Foreign Application Priority Data

Nov. 6, 2006  (JP) ................................. 2006-300323

(51) Int. Cl.
*A61B 5/0476* (2006.01)
*A61B 5/0484* (2006.01)

(52) U.S. Cl.
USPC ......................................... 600/544; 600/545

(58) Field of Classification Search
None
See application file for complete search history.

(56) References Cited

U.S. PATENT DOCUMENTS

2006/0101079 A1   5/2006   Morikawa et al.

FOREIGN PATENT DOCUMENTS

| JP | 2002-102190 | 4/2002 |
|---|---|---|
| JP | 2005-034620 | 2/2005 |
| JP | 2005312605 | 11/2005 |
| JP | 3786952 | 3/2006 |
| JP | 2006-110234 | 4/2006 |
| WO | 03/050782 | 6/2003 |
| WO | 2005/001677 | 1/2005 |

OTHER PUBLICATIONS

Salvaris et al. Proceed IEEE, Aug. 2007.*
Gurrera et al, Psychiatry Research, 2005, vol. 133, pp. 215-228.*
Friedman et al, Neuroscience and Biobehavior Reviews, 2001, vol. 25, pp. 355-373.*
Wright et al, Behavior Genetics, 2001, vol. 31, pp. 555-565).*
International Search Report for corresponding Application No. PCT/JP2007/069451 mailed Nov. 6, 2007.
Emanuel Donchin et al., "The Mental Prosthesis: Assessing the Speed of a P300-Based Brain-Computer Interface", IEEE Transactions on Rehabilitation Engineering, vol. 8, No. 2, Jun. 2000, pp. 174-179.
Hiroshi Nittono, "Event-Related Potential Guidebook for Psychology", Kitaoji Shobo, 2005, pp. 30-33 with English translation of concise explanation.
Spencer Wetter et al., "Olfactory, auditory, and visual ERPs from single trials: no evidence for habituation", International Journal of Psychophysiology, 54, 2004, pp. 263-272.
Shin Seirishinrigaku (or "New Physiopsychology"), vol. 2, Seirishinrigaku No Oyobunya (or "Fields of Application of Physiopsychology"), Sep. 20, 2007, published by Kitaoji Shobo, ISBN 4-7628-2094-6, pp. 14-15, with partial English translation.
Jishoukanrendeni (ERP) Manyuaru—P300 Wo Chushinni (or "Event-Related Potential (ERP) Manual-mainly concerning P300-"), published by Shinohara Shuppan Shinsha, Nov. 15, 1995, ISBN 4-87949-148-9, pp. 254-255 with a partial English translation.

* cited by examiner

*Primary Examiner* — Karen Canella
(74) *Attorney, Agent, or Firm* — Renner, Otto, Boisselle & Sklar, LLP

(57) ABSTRACT

In a system having an interface that utilizes an electroencephalogram, there is realized a calibration which prevents overlooking of calibrational stimulations concerning the electroencephalogram and which is highly accurate.
An electroencephalogram interface system (1) includes an interface section (100) which acquires an electroencephalogram signal from a user, distinguishes a P3 component of a visual event-related potential contained in the electroencephalogram signal after a manipulation menu is presented, and operates a device based on the distinguished P3 component. An electroencephalogram distinction method adjustment apparatus (10) is used for adjusting a distinction method in the interface section (100). Based on a database (13) defining a correlation between a P3 component of an event-related potential obtained from a stimulation to a modality other than the visual sense and a P3 component of a visual event-related potential and on a P3 component of an event-related potential after a stimulation is presented, the apparatus (10) derives a characteristic quantity of the user concerning the P3 component of the visual event-related potential, and adjusts the electroencephalogram distinction method in the interface section (100) based on the characteristic quantity.

14 Claims, 12 Drawing Sheets

| AMPLITUDE | LATENT PERIOD | CORRECTION ZONE |
|---|---|---|
| 1.2倍 | 1.5倍 | 200−500ms |

MODALITY CONVERSION DB 13 (FOR ALL USERS)

(b)

|  | AMPLITUDE | LATENT PERIOD | CORRECTION ZONE |
|---|---|---|---|
| USER A | 1.0 TIMES | 1.3 TIMES | 300−500ms |
| USER B | 1.5 TIMES | 1.6 TIMES | 250−500ms |
| USER C | 1.2 TIMES | 1.4 TIMES | 200−500ms |
| ... | ... | ... | ... |

MODALITY CONVERSION DB 13 (FOR EACH USER)

|  | AMPLITUDE | LATENT PERIOD | ADJUSTMENT ZONE |
|---|---|---|---|
| CHARACTERISTIC QUANTITY ANALYZED BY CALIBRATIONAL ELECTRO-ENCEPHALOGRAM ANALYSIS SECTION 12 | 10μV | 300ms | - |
| STORED CONTENT IN AUDITORY-VISUAL SENSATION CONVERSION DB 13 | 1.2 TIMES | 1.5 TIMES | 200−500ms |
| CORRECTION FOR TEMPLATE | CORRECT SO THAT AMPLITUDE EQUALS 12 (10×1.2) μV | CORRECT SO THAT LATENT PERIOD EQUALS 450 (300×1.5) ms | CORRECT BETWEEN 200-500 ms |

(b)

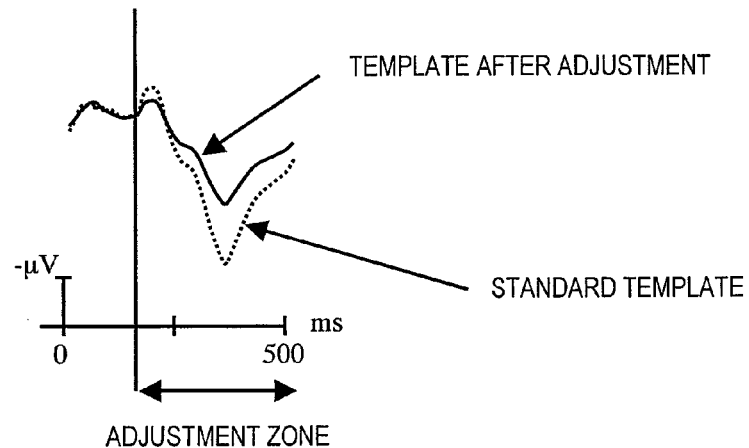

|  | AMPLITUDE | LATENT PERIOD | ADJUSTMENT ZONE |
|---|---|---|---|
| CHARACTERISTIC QUANTITY ANALYZED BY CALIBRATIONAL ELECTRO-ENCEPHALOGRAM ANALYSIS SECTION 12 | 10μV | 300ms | - |
| STORED CONTENT IN AUDITORY-VISUAL SENSATION CONVERSION DB 13 | 1.2 TIMES | 1.5 TIMES | 200-500ms |
| STANDARD TEMPLATE STORED IN ELECTROENCEPHALOGRAM IF SECTION 100 | 20μV | 450ms | - |
| ADJUSTMENT FOR EVENT-RELATED POTENTIAL MEASURED BY BIOLOGICAL SIGNAL MEASUREMENT SECTION 50 | 20/(10*1.2)=1.67 TIMES | NO CORRECTION | CORRECT BETWEEN 200-500 ms |

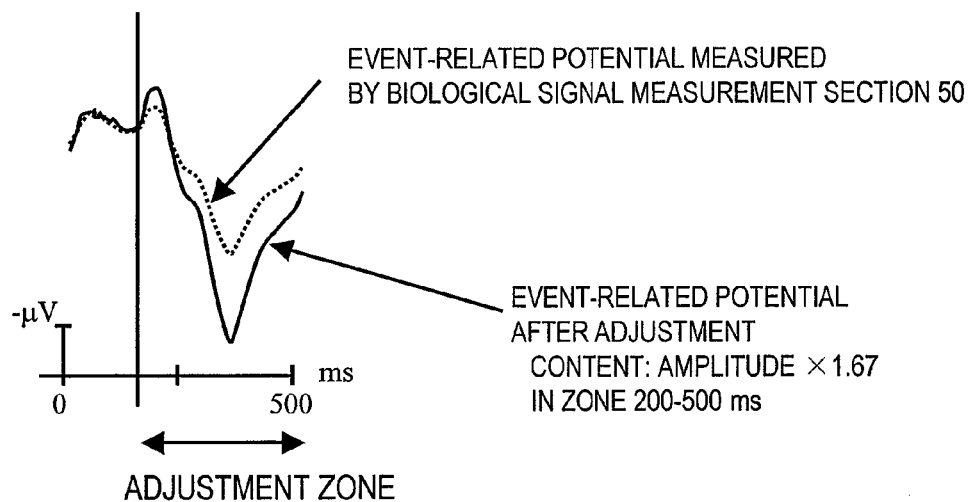

| AMPLITUDE | LATENT PERIOD | CORRECTION ZONE |
|---|---|---|
| 1.3 TIMES | 1.1 TIMES | 200−500ms |

SOMATIC-VISUAL SENSATION CONVERSION DB 32 (FOR ALL USERS)

(b)

|  | AMPLITUDE | LATENT PERIOD | CORRECTION ZONE |
|---|---|---|---|
| USER A | 1.0 TIMES | 0.8 TIMES | 300−450ms |
| USER B | 0.9 TIMES | 1.2 TIMES | 250−500ms |
| USER C | 1.2 TIMES | 1.0 TIMES | 200−400ms |
| ... | ... | ... | ... |

SOMATIC-VISUAL SENSATION CONVERSION DB 32 (FOR EACH USER)

BRAIN WAVE IDENTIFICATION METHOD ADJUSTING DEVICE AND METHOD

TECHNICAL FIELD

The present invention relates to an interface (electroencephalogram interface) system which allows a device to be manipulated by utilizing an electroencephalogram. More specifically, it relates to an electroencephalogram interface system having an apparatus which measures the electroencephalogram of a user in real time and performs calibration for enabling precise analysis.

BACKGROUND ART

In recent years, various types of information devices such as television sets, mobile phones, PDAs (Personal Digital Assistants) have gained prevalence and entered into people's lives. Thus, users need to manipulate information devices in many scenes of their usual lives. Usually, in realizing a device manipulation, a user utilizes a hand to input an input command via an input means (interface section) such as a button. However, in situations where both hands are full because of tasks other than a device manipulation, e.g. household chores, rearing of children, or driving, it is difficult to make an input by using an interface section and it is impossible to realize a device manipulation. Therefore, there are increasing needs of users to manipulate information devices in every kind of situation.

In answer to such needs, input means utilizing biological signals from a user has been developed. For example, Non-Patent Document 1 discloses a technique that utilizes an event-related potential of electroencephalogram for distinguishing an option which a user wishes to select. To specifically describe the technique described in Non-Patent Document 1, options are randomly highlighted, and a P3 component of an event-related potential which appears about 300 ms after a point in time that an option was highlighted is utilized to enable distinction of the option which the user wishes to select. According to this technique, a user is able to identify an option which he or she wishes to select, without using a hand.

As used herein, an "event-related potential" refers to a transient potential fluctuation in the brain which occurs in temporal relationship with an external or internal event. An electroencephalogram interface section 100 utilizes an event-related potential which is obtained from a stimulation to the visual sense as an external event. For example, within the event-related potential for a visual stimulation, a so-called P3 component may be utilized to perform processing such as switching of channels, selection of a program genre of which viewing is desired, and sound volume level adjustment. The "P3 component" refers to a positive component of the event-related potential which appears in a time slot of 250 ms to 500 ms after a target stimulation is presented, regardless of the type of sensory stimulation such as auditory sense, visual sense, or somatic sensation.

For an application of the event-related potential to an interface, it is important to distinguish the event-related potential (e.g., the visual P3 component) of a subject with a high accuracy. Therefore, it is necessary to accurately measure a biological signal and accurately distinguish the measured biological signal with an appropriate distinction technique.

In order to accurately measure a biological signal, it is commonplace to calibrate the measurement equipment so that the data which is measured with the measurement equipment is adjusted to accurately present the biological information of a user. For example, Patent Document 1 discloses a technique which, in order to accurately measure the line of sight of a user, calibrates the measurement equipment before measuring the line of sight, and establishes a matched coordinate system between the measurement equipment and the line of sight of the user.

On the other hand, appropriate distinction methods have been devised which account for individual differences appearing in the components of the event-related potential. For example, Patent Document 2 discloses a technique which provides an improved distinction ratio by changing the distinction method for every user. Rather than applying a single criterion to the distinctions for all users, this technique previously generates a template for each individual from an arithmetic mean waveform of an event-related potential regarding a situation to be examined, and distinguishes a component of the event-related potential by using the template. For details concerning individual differences in the event-related potential, see Non-Patent Document 2, for example.

[Patent Document 1] Japanese Laid-Open Patent Publication No. 2005-312605
[Patent Document 2] The pamphlet of International Laid-Open No. 05/001677
[Non-Patent Document 1] Emanuel Donchin and two others, "The Mental Prosthesis: Assessing the Speed of a P300-Based Brain-Computer Interface", TRANSACTIONS ON REHABILITATION ENGINEERING 2000, Vol. 8, June 2000
[Non-Patent Document 2] Hiroshi NITTONO, "Event-Related Potential Guidebook For Psychology", Kitaoji Shobo, 2005, p. 32

DISCLOSURE OF INVENTION

Problems to be Solved by the Invention

One conceivable calibration method for accurately measuring an electroencephalogram may be to purposely create a situation for distinction and allow the user to select from a dummy menu when an electroencephalograph is worn, for example. Since the electroencephalograph is calibrated on the assumption that the electroencephalogram at the time of menu selection represents the biological information of the user when a desired menu is presented, it is possible to adjust for differences in waveform that are associated with variations in measurement conditions such as conditions of the electrodes worn, e.g., the electrical resistance of the scalp and positions of the electrodes worn.

However, when an electroencephalogram is to be utilized for an interface, the electroencephalogram is measured for a long time (in some case a whole day). Thus, changes may occur in the manner in which the electrodes are worn, e.g., the electrode positions may be shifted due to perspiration or physical motions. Therefore, accurate measurement of a biological signal cannot be realized with only a calibration performed at the time of wearing the electroencephalograph. On the other hand, even though the above-mentioned regular calibrations are necessary for measuring changes in the manner in which the electrodes are worn, the calibrations will be cumbersome to the user, and performing regular calibrations will add to the burden on the user.

Moreover, components of the event-related potential are known to change depending on the arousal level. In a situation where the electroencephalogram is being measured all day long, it is considered that the arousal level of the user will change between morning and night, for example. Especially when the arousal level is low, the amplitude will decrease and the difficulty level of distinction will increase, thus making it necessary to change the criterion of distinction. While being effective for correcting errors of the measurement equipment, the conventional calibration method cannot measure states of the user such as the arousal level, and thus is unable to change the criterion of distinction based on the arousal level of the user.

In addition, when manipulating a device with an electroencephalogram interface, the visual P3 component corresponding to menu items which are visually presented is used, and therefore a visual stimulation is conventionally presented as a stimulation for calibration purposes. However, under interface conditions, there is no guarantee that the user is paying his or her attention to the calibration stimulation, e.g., when manipulating a television set while eating, thus leading to a problem in that an accurate calibration cannot be performed.

All of these problems were beyond expectation from any experimentation under laboratory-room conditions, and were first recognized when contemplating measuring an electroencephalogram on a daily basis and using it for an interface.

An objective of the present invention is, in a system having an interface that utilizes an electroencephalogram, to ensure that a user will not overlook a calibrational stimulation when a calibration is performed while taking into consideration the user's state and the manner in which the electrodes for electroencephalogram measurement are worn. It is also an objective of the present invention to realize a highly accurate distinction by adjusting the distinction method for a visual P3 component to be used in an electroencephalogram interface, on the basis of a P3 component of an event-related potential that corresponds to a calibrational stimulation.

Means for Solving the Problems

In an electroencephalogram interface system having an output section for visually presenting a manipulation menu for a device, a biological signal measurement section for acquiring an electroencephalogram signal from a user, and an electroencephalogram interface section for, by using a pre-stored parameter of visual event-related potential, distinguishing a P3 component of a visual event-related potential contained in an electroencephalogram signal after the manipulation menu is presented, and operating the device based on the distinguished P3 component, an electroencephalogram distinction method adjustment apparatus according to the present invention is used for adjusting a distinction method in the electroencephalogram interface section. The electroencephalogram distinction method adjustment apparatus comprises: a database defining a correlation between a P3 component of an event-related potential obtained from a stimulation to a modality other than the visual sense and a P3 component of a visual event-related potential; a stimulation presentation section for presenting the stimulation via the output section; an analysis section for analyzing an event-related potential contained in the electroencephalogram signal after the stimulation is presented; and a distinction method adjustment section for deriving a characteristic quantity of the user concerning a P3 component of a visual event-related potential based on a P3 component of the analyzed event-related potential and the database, and adjusting the electroencephalogram distinction method in the electroencephalogram interface section based on the characteristic quantity.

The stimulation presentation section may present an auditory stimulation as the stimulation.

The stimulation presentation section may present a somatic stimulation as the stimulation.

The electroencephalogram interface section may distinguish presence or absence of a P3 component of a visual event-related potential of the user based on a threshold value which is set as the parameter; and the distinction method adjustment section may adjust the threshold value based on the characteristic quantity.

The electroencephalogram interface section may distinguish presence or absence of a P3 component of a visual event-related potential of the user based on a template waveform of visual event-related potential which is set as the parameter; and the distinction method adjustment section may adjust the template based on the characteristic quantity.

The distinction method adjustment section may adjust an electroencephalogram signal of the user based on the characteristic quantity.

The electroencephalogram interface section may distinguish presence or absence of a P3 component of the visual event-related potential based on a threshold value concerning amplitude of visual event-related potential; the database may define a correlation concerning amplitude of the P3 component; and the distinction method adjustment section may adjust the threshold value based on a characteristic quantity concerning amplitude.

The database may define a correlation concerning amplitude of the P3 component; and the distinction method adjustment section may adjust the template based on a characteristic quantity concerning amplitude.

The database may define a correlation concerning amplitude of the P3 component; and the distinction method adjustment section may adjust the electroencephalogram signal based on a characteristic quantity concerning amplitude.

The stimulation presentation section may present a stimulation when use of the electroencephalogram interface system is begun.

The stimulation presentation section may present the stimulation at a random point in time during a period in which the electroencephalogram interface system is being used.

In an electroencephalogram interface system having an output section for visually presenting a manipulation menu for a device, a biological signal measurement section for acquiring an electroencephalogram signal from a user, and an electroencephalogram interface section for, by using a pre-stored parameter of visual event-related potential, distinguishing a P3 component of a visual event-related potential contained in an electroencephalogram signal after the manipulation menu is presented, and operating the device based on the distinguished P3 component, a method for adjusting a distinction method for an electroencephalogram according to the present invention is used for adjusting a distinction method for an electroencephalogram in the electroencephalogram interface section. The method comprises the steps of: providing a database defining a correlation between a P3 component of an event-related potential obtained from a stimulation to a modality other than the visual sense and a P3 component of a visual event-related potential; presenting the stimulation via the output section; analyzing an event-related potential contained in the electroencephalogram signal after the stimulation is presented; deriving a characteristic quantity of the user concerning a P3 component of a visual event-related potential based on a P3 component of the analyzed event-related potential and the database; and adjusting the electroencephalogram distinction method in the electroencephalogram interface section based on the characteristic quantity.

Effects of the Invention

With an apparatus and method for distinction method adjustment according to the present invention and an electroencephalogram interface system incorporating the distinction method adjustment apparatus, a distinction method for a visual P3 component which is used for a distinction in the electroencephalogram interface system is adjusted by using a P3 component of an event-related potential which is obtained from a stimulation to a modality other than the visual sense. This prevents overlooking of calibrational stimulations, which would present a problem in an interface which constantly measures an electroencephalogram, and eliminates influences of an individual user's state such as physical condition and changes in the manner in which electrodes for electroencephalogram detection are worn, thus making it possible to accurately measure an electroencephalogram and maintain a high distinction ratio. As a result, device operations that are not intended by the user, which are ascribable to incorrect distinctions of the electroencephalogram, are reduced, whereby an improved manipulability of the electroencephalogram interface is realized.

BRIEF DESCRIPTION OF DRAWINGS

FIGS. 5 (a) and (b) are each a diagram showing an exemplary data structure of a modality conversion DB.

FIGS. 6 (a) and (b) are diagrams showing an exemplary adjustment for a distinction method, by overwriting a template.

FIGS. 7 (a) and (b) are diagrams showing an exemplary adjustment for a distinction method, by changing the magnification of an electroencephalogram signal.

FIGS. 16 (a) and (b) are each a diagram showing an exemplary data structure of a conversion DB 32.

Figure 1:
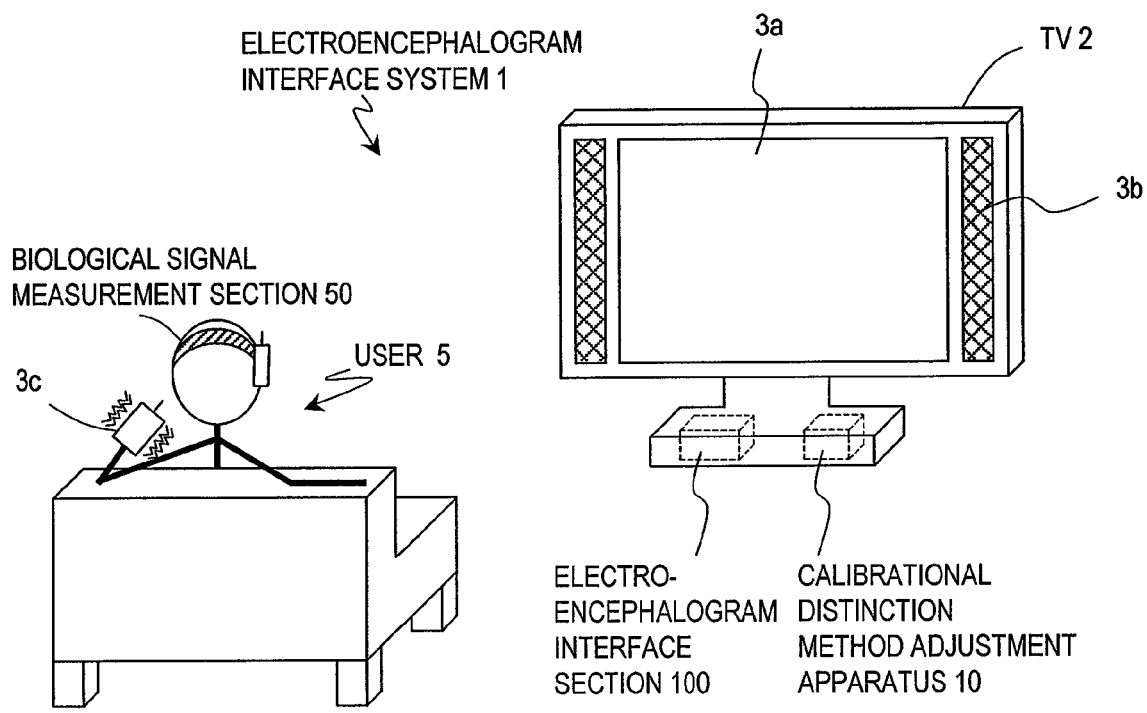
FIG. 1 A diagram showing a construction and an environment of use for an electroencephalogram interface system 1.

DESCRIPTION OF REFERENCE NUMERALS 1 electroencephalogram interface system
3 output section
3a screen
3b loudspeaker
10 distinction method adjustment apparatus
11 calibrational stimulation presentation section
12 calibrational electroencephalogram analysis section
13 modality conversion database
14 distinction method adjustment section
50 biological signal measurement section
100 electroencephalogram interface section

BEST MODE FOR CARRYING OUT THE INVENTION

Hereinafter, with reference to the attached drawings, embodiments of an electroencephalogram interface system and a distinction method adjustment apparatus to be incorporated in an electroencephalogram interface system according to the present invention will be described.

Hereinafter, the electroencephalogram interface system will be first described, followed by a description of the construction and operation of the distinction method adjustment apparatus.

FIG. 1 illustrates a construction and an environment of use for the electroencephalogram interface system 1. The electroencephalogram interface system 1 is exemplified so as to correspond to a system construction of Embodiment 1 described later.

The electroencephalogram interface system 1 is a system for providing an interface for manipulating a TV 2 by utilizing an electroencephalogram signal from a user 5. An electroencephalogram signal from the user 5 is acquired by a biological signal measurement section 50 which is worn on the head of the user, and transmitted to an electroencephalogram interface section 100 in a wireless or wired manner. The electroencephalogram interface section 100 internalized in the TV 2 recognizes an intent of the user by utilizing a component called an event-related potential, which constitutes a part of the electroencephalogram, and performs processes such as switching of channels.

Figure 2:
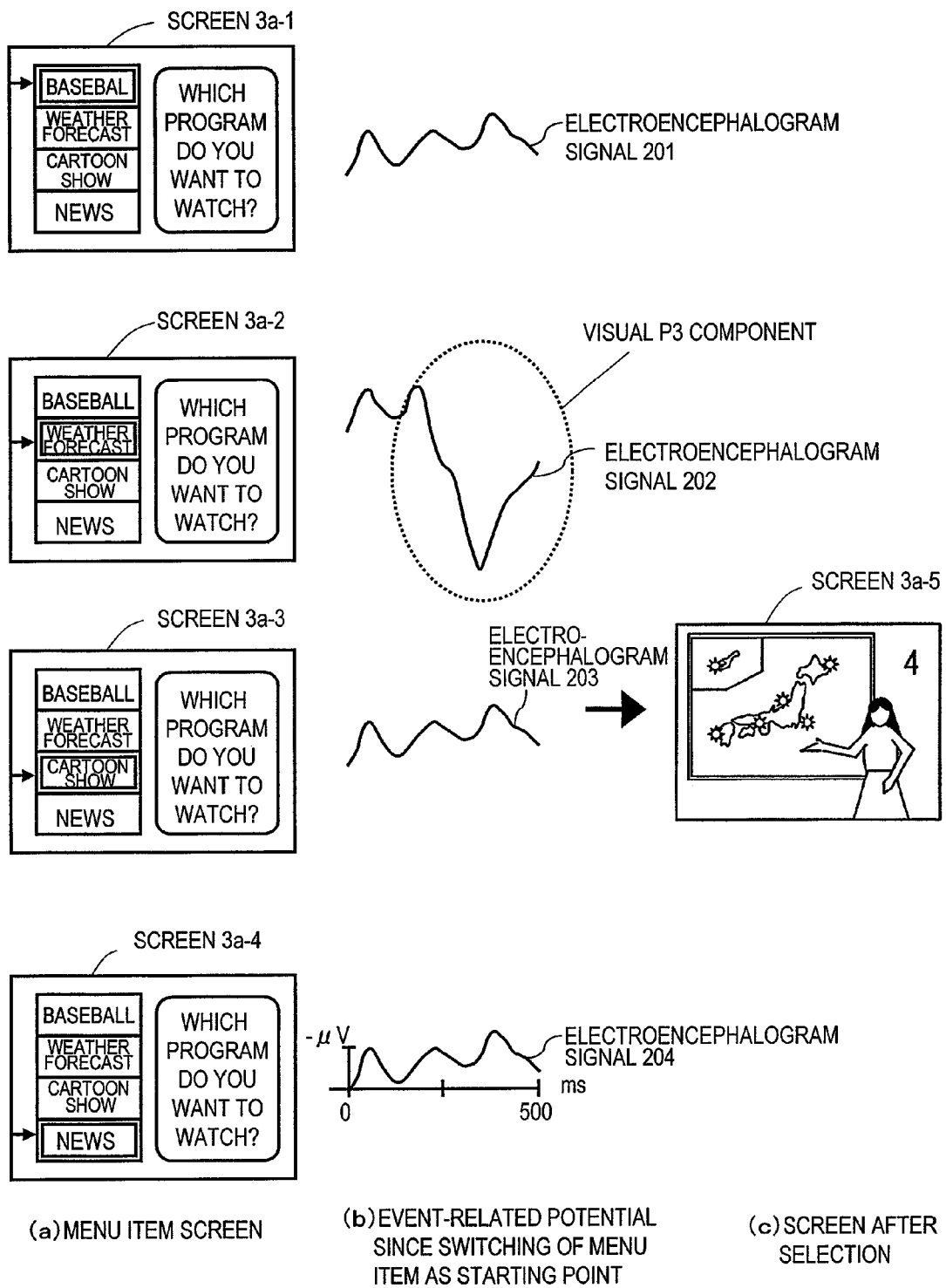
FIG. 2 (a) to (c) are diagrams showing an example where a TV 2 is manipulated in the electroencephalogram interface system 1 and a user 5 watches a program of a genre which he or she wishes to view.

FIG. 2 shows an example where the TV 2 is manipulated in the electroencephalogram interface system 1 and the user 5 watches a program of a genre which he or she wishes to view.

FIG. 2(a) shows exemplary menu items which the electroencephalogram interface section 100 presents to the user via a screen 3a of the TV 2. In FIG. 2(a), a screen 3a-1 to a screen 3a-4 respectively illustrate how menu items "baseball", "weather forecast", "cartoon show", and "news" are highlighted in order or at random. By highlighting menu items, it becomes possible to measure the event-related potential since a point of highlighting each menu item as a starting point. Note that, instead of highlighting, or in addition to highlighting, a menu item may be presented by a point using an auxiliary arrow.

FIG. 2(b) schematically shows the event-related potential of an electroencephalogram signal from the user which is measured since a point of highlighting a menu item as a starting point. It is assumed that the user is currently wishing to watch "weather forecast". Among electroencephalogram signals 201 to 204 respectively corresponding to the screen 3a-1 to the screen 3a-4, if the user 5 looks at the screen 3a-2 in which "weather forecast" is highlighted, a characteristic positive component appears with a latent period of about 400-450 ms since the point of highlighting "weather forecast" as a starting point (Non-Patent Document 1).

When the electroencephalogram interface section 100 distinguishes this appearance of the visual P3 component, selection of the menu item "weather forecast" which the user wishes to select becomes possible. FIG. 2(c) shows the screen 3a-5, which comes after the channel has been switched to "weather forecast" as a result of distinguishing the visual P3 component.

Figure 3:
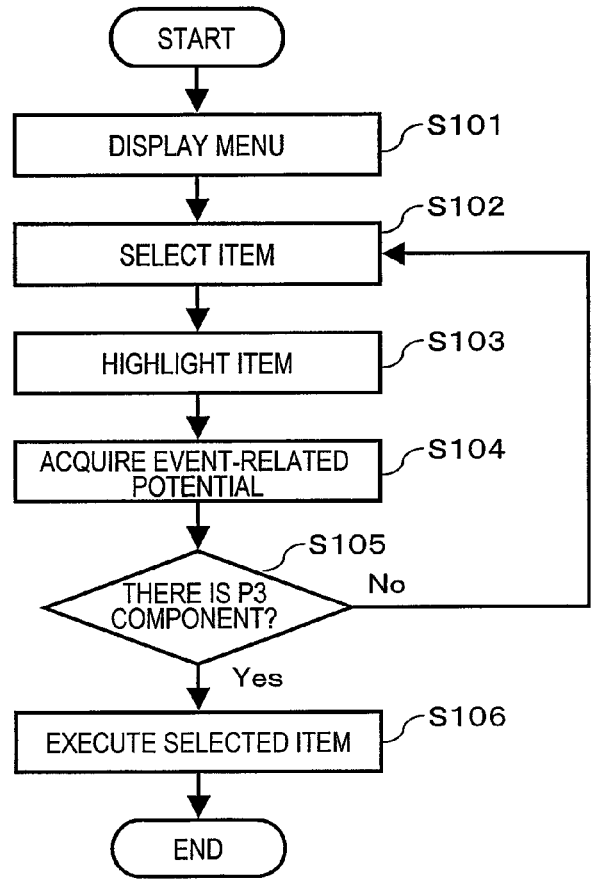
FIG. 3 A flowchart showing a procedure of processing by an electroencephalogram interface.

FIG. 3 shows an example of a processing procedure by the electroencephalogram interface. At step S101, the electroencephalogram interface section 100 presents menu items (FIG. 2(a)). At step S102, the electroencephalogram interface section 100 selects one of the menu items. At step S103, the menu item selected at step S102 is highlighted.

At step S104, the electroencephalogram interface section 100 measures the event-related potential of the user for the duration of e.g. 500 ms since the point of highlighting a menu item at step S103 as a starting point. Herein, event-related potentials 201 to 204 of the electroencephalogram signals schematically shown in FIG. 2(b) are measured.

At step S105, distinction is made as to whether the visual P3 component is contained in the event-related potential measured at step S104 or not. Distinction of the visual P3 component may be made by simply subjecting the waveform to threshold processing, or as described in Patent Document 2, a correlation coefficient may be calculated with respect to a template which is generated from an arithmetic mean waveform of the visual P3 component that has been measured with respect to each user in advance. If Yes at step S105, control proceeds to step S106; if No, control returns to step S102 and the next menu item is selected.

At step S106, the electroencephalogram interface section 100 executes a process corresponding to the menu item selected at step S105. As a result, that menu item is selected and executed, whereby the screen 3a-5 shown in FIG. 2(c) is displayed.

In accordance with the electroencephalogram interface system 1 as such, the user is able to manipulate a device such as the TV 2 without using a hand, even in the case where their both hands are full due to a household chore or rearing of children, for example. Thus, the manipulability of the device is significantly improved.

In step S105 above, the time and amplitude with which the visual P3 component appears in the electroencephalogram signal (event-related potential) may fluctuate from user to user, and therefore it would be inappropriate to universally distinguish the appearance of a visual P3 component by using a fixed threshold value or the like. Therefore, in order to realize a process based on an event-related potential, it is necessary to adjust the criterion of operating in accordance with the signal from the user 5 in the electroencephalogram interface system 1. This operation is the so-called calibration. The calibration is performed by the distinction method adjustment apparatus 10 shown in FIG. 1.

The distinction method adjustment apparatuses which are described in the following embodiments present to the user 5 a stimulation for any modality other than the visual sense (the five senses other than the visual sense) that is sure to produce a response to the event-related potential, e.g., a stimulation to the auditory sense by utilizing loudspeakers 3b or a stimulation to the somatic sensation by utilizing a vibrator 3c, and measure an event-related potential of the electroencephalogram after this presentation. The event-related potential of the electroencephalogram is transmitted to the distinction method adjustment apparatus 10 in a wireless or wired manner.

The reason for utilizing a stimulation to a modality other than the visual sense is in order to surely perform a calibration without allowing a calibrational stimulation to be overlooked. This is based on the fact that, if a calibration is performed based only on the visual sense, the user may overlook the visual stimulation.

Below-described Embodiments 1 and 2 will illustrate examples where an auditory stimulation is adopted as a calibrational stimulation, whereas Embodiment 3 will illustrate an example where a somatic stimulation is adopted. However, the calibrational stimulation to be presented is not limited to one type, and a plurality of types of stimulations may be simultaneously presented. Alternatively, the stimulation type may be switched based on a suitable criterion.

It is known that, for each test subject, there is a positive correlation between the P3 component of an event-related potential which is obtained with a stimulation to a modality other than the visual sense (e.g., auditory P3 component, olfactory P3 component) and the P3 component of the visual event-related potential, with respect to the amplitude and latent period. Moreover, part of the differences in the event-related potential from test subject to test subject is ascribed to individual anatomical differences such as the shape of the cranium and the brain, and it is also considered that a correlation exists between the visual P3 component and the somatic P3 component with respect to the amplitude and latent period. Moreover, according to the disclosure of Kaga et al., "Event-Related Potential (ERP) Manual-mainly concerning P300-", Shinohara Shuppan Shinsha, 1995; p. 255, it is known that the amplitude and latent period of the P3 will change depending on the arousal level of the user, even within the same user.

Usually, when making a distinction between two types of stimulations appearing with different frequencies, a P3 component of the event-related potential will appear for the stimulation appearing with the lower frequency. However, as is described in Kakinoki et al., "New Physiopsychology Vol. 2", Kitaoji Shobo, 1997, p. 15, it is also known to appear when one type of stimulation of the same tonal pitch is presented.

By utilizing the correlation between the P3 component of an event-related potential for an auditory or somatic stimulation and the P3 component of a visual event-related potential, it becomes possible to derive a characteristic quantity(s) of the user 5 concerning the P3 component of the visual event-related potential. Based on the characteristic quantity(s), the distinction method adjustment apparatus 10 adjusts the electroencephalogram distinction method in the electroencephalogram interface section 100.

The timing with which to perform the calibration is when beginning use of the electroencephalogram interface system 1, or when a predetermined time has elapsed since the beginning of use. Alternatively, the calibration may be performed with random timing. Since it is possible to adjust the distinction method for the electroencephalogram in accordance with the user's state and the manner in which the electrodes are worn in each case, the distinction ratio of the electroencephalogram interface is improved.

Embodiment 1

Figure 4:
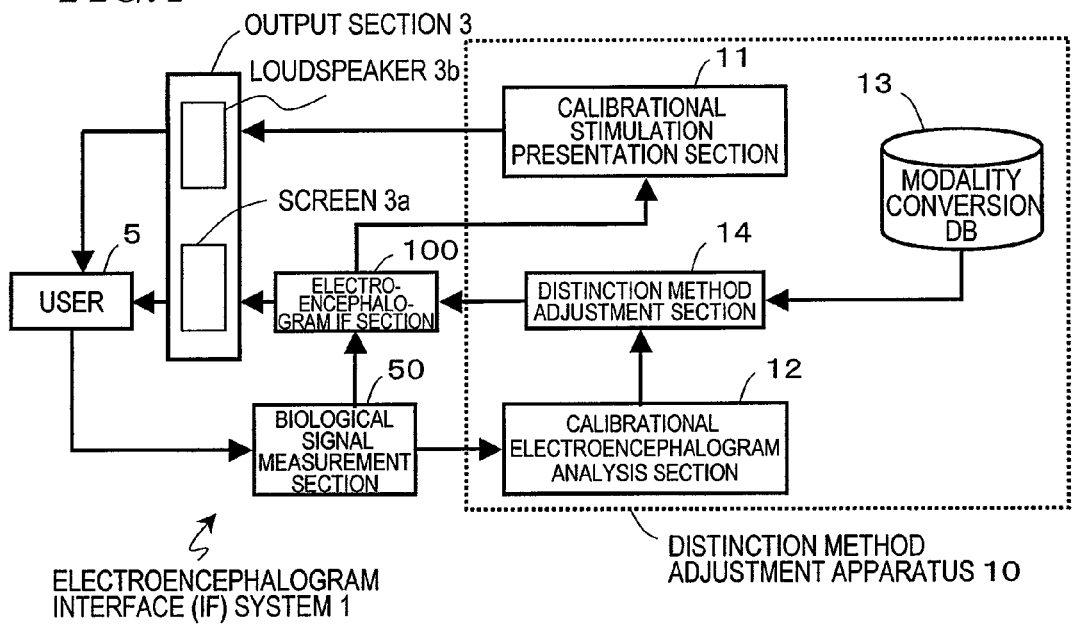
FIG. 4 A diagram showing a functional block construction of an electroencephalogram interface system 1 according to Embodiment 1.

FIG. 4 shows a functional block construction of the electroencephalogram interface system 1 according to the present embodiment. The electroencephalogram interface system 1 includes an output section 3, a distinction method adjustment apparatus 10, a biological signal measurement section 50, and an electroencephalogram interface (IF) section 100. FIG. 4 also shows detailed functional blocks of the adjustment apparatus 10. The user 5 block is illustrated for convenience of explanation.

The output section 3 includes a screen 3a and loudspeakers 3b.

In the present embodiment, as a calibrational stimulation, an auditory stimulation is presented from the loudspeakers 3b at the same time as displaying menu items on the screen 3a, and the distinction method for the visual P3 component in the electroencephalogram interface is adjusted by using the P3 component of an event-related potential for the auditory stimulation for calibration purposes. This enables a distinction which is in accordance with the user's state and the manner in which the electrodes are worn immediately before manipulating the electroencephalogram interface, whereby the distinction ratio of the visual P3 component to be used in the electroencephalogram interface is improved.

The user 5 is merely looking at menu items (options) concerning device manipulations which are presented by the electroencephalogram interface section 100 on the screen 3a, and does not make any manipulation input. However, the device operates in accordance with the menu item which is selected via the electroencephalogram interface section 100. Note that displaying of a menu item, i.e., a visual stimulation, is not an essential requirement. The content of the menu item may be output as an audio from the loudspeakers 3b.

The distinction method adjustment apparatus 10 is connected to the biological signal detection section 50 and the electroencephalogram interface section 100 in a wireless or wired manner, and performs transmission and reception of signals. Although FIG. 4 illustrates the biological signal detection section 50 and the electroencephalogram interface section 100 as separate entities from the distinction method adjustment apparatus 10, this is only exemplary. A part or whole of the biological signal detection section 50 and the electroencephalogram interface section may be provided within the distinction method adjustment apparatus 10.

The biological signal detection section 50 is an electroencephalograph which detects a biological signal of the user 5, and measures electroencephalogram as a biological signal. The electroencephalograph may a head-mounted electroencephalograph as shown in FIG. 1. It is assumed that the user 5 has put on the electroencephalograph in advance.

Electrodes are disposed on the biological signal measurement section 50 so that, when worn on the head of the user 5, the electrodes come into contact with the head at predetermined positions. The positioning of the electrodes may be, for example, Pz (median parietal), A1 (earlobe), and the nasion of the user 5. However, it will suffice if there are at least two electrodes, and potential measurement will be possible with only Pz and A1, for example. These electrode positions are to be determined based on reliability of signal measurements, wearing ease, and the like.

Thus, the biological signal measurement section 50 is able to measure the event-related potential of the user 5. The measured electroencephalogram of the user 5 are sampled so as to be computer-processible, and are sent to the electroencephalogram interface section 100 and the distinction method adjustment apparatus 10. Note that, in order to reduce the influence of noises which may be mixed in the electroencephalogram, the electroencephalogram to be measured in the biological signal measurement section 50 are subjected to band-pass filtering from e.g. 0.05 to 20 Hz in advance, and to baseline correction with respect to an average potential at e.g. 200 milliseconds before a menu item or an auditory stimulation is presented.

The electroencephalogram interface section 100 presents menu items concerning device manipulations to the user, cuts out the electroencephalogram measured by the biological signal measurement section 50, and subjects it to distinction. Then, it controls the device operation according to the distinction result. The basic operation of the electroencephalogram interface section 100 is as described above.

Assuming that the device to be controlled by using the electroencephalogram interface section 100 is the TV 2 shown in FIG. 1, for example, the menu items are presented to the user 5 via the screen 3a. As shown in FIG. 2(a), the menu items are highlighted one by one in every predetermined period (e.g. 350 ms). The predetermined interval at which menu items are highlighted may be 200 ms, 500 ms, or 1000 ms.

From the electroencephalogram of the user 5 measured by the biological signal measurement section 50, the electroencephalogram interface section 100 cuts out e.g. 500 ms since the point of highlighting the menu item as a starting point, which is longer than the latent period of the auditory P3 component or visual P3 component, and distinguishes the waveform. The time for which to cut out the electroencephalogram may be 1000 ms. The method of distinguishing the event-related potential may be to simply subject the waveform to threshold processing, or as described in Patent Document 2, a correlation coefficient may be calculated with respect to a template which is generated from an arithmetic mean waveform of the visual P3 component that has been measured with respect to each user in advance. A parameter for the distinction is adjusted by the distinction method adjustment apparatus 10 by a method described later.

Next, the detailed construction of the distinction method adjustment apparatus 10 of the present embodiment will be described. One main feature of the present invention lies in the construction and operation of the distinction method adjustment apparatus 10.

The distinction method adjustment apparatus 10 includes a calibrational stimulation presentation section 11, a calibrational electroencephalogram analysis section 12, a modality conversion database 13, and a distinction method adjustment section 14.

At the same time as the menu item presentation via the screen 3a, the calibrational stimulation presentation section 11 (hereinafter referred to as the "stimulation presentation section 11") presents an auditory stimulation for calibration purposes via the loudspeakers 3b.

The calibrational electroencephalogram analysis section 12 (hereinafter referred to as the "electroencephalogram analysis section 12") analyzes an event-related potential for the calibrational auditory stimulation as measured by the biological signal measurement section 50.

The modality conversion database (DB) 13 defines a correlation between the auditory P3 component and the visual P3 component. Note that the modality conversion DB 13 may be recorded and stored on any arbitrary storage medium. For example, the modality conversion DB 13 may be recorded on a hard disk or a semiconductor memory such as a ROM, an SRAM, or a flash memory.

Based on the result as analyzed by the electroencephalogram analysis section 12, or specifically, based on the P3 component of the event-related potential obtained responsive to the auditory stimulation, the distinction method adjustment section 14 derives a characteristic quantity(s) of the user concerning the P3 component of the visual event-related potential by referring to the modality conversion DB 13. Then, based on the characteristic quantity(s), it adjusts the electroencephalogram distinction method in the electroencephalogram interface section 100. The adjustment of the electroencephalogram distinction method is a process of determining a parameter to be used for the distinction of the P3 component of the visual event-related potential stored in the electroencephalogram interface section 100 and sending it to the electroencephalogram interface section 100 in order to update that parameter.

Hereinafter, the respective component elements of the distinction method adjustment apparatus 10 will be described more specifically.

At the same time as the menu item presentation, the stimulation presentation section 11 presents a calibrational auditory stimulation to the user 5. The auditory stimulation may be a simple sound, e.g., a 1000 Hz toneburst, or a sound which will evoke an image of a device's operating sound, e.g., a "pong". Without being limited to one kind of sound, it may be a plurality of kinds of sounds.

The electroencephalogram analysis section 12 analyzes the characteristic quantity(s) by utilizing an electroencephalogram for the duration of e.g. 500 ms since a starting point which is the timing of the stimulation presentation section 11 presenting a calibration stimulation, within the electroencephalogram of the user 5 as measured by the biological signal measurement section 50. The characteristic quantities to be analyzed may be the amplitude and latent period of the P3 component responsive to an auditory stimulation, for example.

As described above, because the event-related potential has a low S/N ratio, a 2 Hz low-pass filter may be used for the event-related potential, for example, in order to analyze the amplitude and latent period of the P3 component responsive to an auditory stimulation.

As a zone in which to analyze the characteristic quantity(s), for example, a 100 ms time slot in the neighborhood of 300 ms after presentation of a stimulation, which is generally believed to produce a P3 component responsive to an auditory stimulation, may also be used. The latent period and amplitude may be determined by utilizing a positiveness peak within that time slot. Note that, in the case where a large noise such as an electro-oculographic potential is mixed in the electroencephalogram immediately after presentation of a calibrational auditory stimulation, such that it is impossible to perform a correct calibration, the distinction method may be adjusted by using an immediately previous calibration result, or the distinction method may not be adjusted at all.

Next, the modality conversion DB 13 will be described. FIGS. 5(*a*) and (*b*) are each a diagram showing an exemplary data structure of the modality conversion DB. The modality conversion DB 13 is used in order to convert an event-related potential (auditory event-related potential) obtained responsive to an auditory stimulation into an event-related potential (visual event-related potential) obtained responsive to a visual stimulation.

The modality conversion DB 13 stores data for adjusting the distinction method for the visual P3 component in the electroencephalogram interface section 100 in accordance with the amplitude and latent period data of the component responsive to an auditory stimulation as determined by the electroencephalogram analysis section 12, e.g., amplitude, latent period, and correction zone.

FIG. 5(*a*) shows a modality conversion DB 13 that defines conversion rules which are commonly applied to all users. According to this modality conversion DB 13, in a zone of the auditory event-related potential designated in the "correction zone" column (the zone of 200-500 ms after stimulation presentation), the amplitude and latent period of the auditory event-related potential are to be multiplied by 1.2 and 1.5, respectively. The zone of 200-500 ms after stimulation presentation is a zone containing a P3 component of the event-related potential.

These conversion rules are to be defined based on the data of correlation between the P3 component responsive to auditory stimulations and the P3 component responsive to visual stimulations which is previously acquired through experimentation or the like. Therefore, by performing the aforementioned conversion, a highly-reliable P3 component of a visual event-related potential can be obtained on the basis of an auditory event-related potential. By utilizing this P3 component, it is possible to adjust the distinction method for the visual P3 component in the electroencephalogram interface section 100 described below.

On the other hand, FIG. 5(*b*) shows a modality conversion DB 13 that defines conversion rules which are switchably applied to different users by measuring a conversion criterion for each user in advance. The conversion rules to be applied are identified and switched by separately inputting information identifying a user such as a user name, for example. The method of conversion is the same as in the method of conversion described in connection with FIG. 5(*a*) above.

By referring to the modality conversion DB 13, it is possible to obtain the amplitude and latent period of a visual event-related potential from the amplitude and latent period of an auditory event-related potential. By designating as a correction zone a zone which contains a P3 component, it is possible to identify the P3 component of a visual event-related potential as a characteristic quantity(s) of that user.

By referring to the amplitude and latent period of an auditory P3 component responsive to the calibration stimulation as analyzed by the electroencephalogram analysis section 12 and the DB which is stored in the modality conversion DB 13 for adjusting the distinction method for a visual P3 component from an auditory P3 component, the distinction method adjustment section 14 overwrites a parameter for distinguishing an event-related potential in the electroencephalogram interface section 100. Various parameters are possible. For example, in the case where the electroencephalogram interface section 100 distinguishes a visual P3 component by subjecting a waveform to threshold processing, the distinction method may be adjusted by overwriting a threshold value as a parameter. In the case where a template is generated from an arithmetic mean waveform of visual P3 components which are measured with respect to different users and the visual P3 component is distinguished by using that template, the distinction method may be adjusted by overwriting this template having been set as a parameter.

FIGS. 6(*a*) and (*b*) show an exemplary adjustment for the distinction method by overwriting a template. FIG. 6(*a*) shows data to be used for adjusting the distinction method, and calculation formulae for template adjustment. As the data, characteristic quantities concerning the amplitude and latent period of an auditory P3 component as analyzed by the electroencephalogram analysis section 12, and the correlation data between the auditory P3 component and the visual P3 component as stored in the modality conversion DB 13 are used. Then, a parameter for template adjustment is calculated by applying multiplication to the data concerning the amplitude and latent period each. FIG. 6(*b*) also shows a standard template waveform which has been adjusted with a template correction parameter calculated from FIG. 6(*a*). It can be seen that the waveform of the template is adjusted in the adjustment zone of 200-500 ms. As used herein, the "waveform" refers to the amplitude and latent period of the template waveform.

Moreover, without changing the threshold value or the template, the electroencephalogram interface section 100 may perform a distinction through an adjustment using a method such as multiplying the electroencephalogram signal measured by the biological signal measurement section 50 with a certain magnification based on the distinction method adjustment section 14.

FIGS. 7(*a*) and (*b*) show an exemplary adjustment for the distinction method by changing the magnification of the electroencephalogram signal. FIG. 7(*a*) shows data to be used for adjusting the distinction method, and calculation formulae for template adjustment. As the data, characteristic quantities concerning the amplitude and latent period of an auditory P3 component as analyzed by the electroencephalogram analysis section 12, the correlation data between the auditory P3 component and the visual P3 component as stored in the modality conversion DB 13, and characteristic quantities concerning the amplitude and latent period of a standard template stored in the electroencephalogram interface section 100 are used. Then, a parameter for adjusting the electroencephalogram signal measured by the biological signal measurement section 50 is calculated by dividing characteristic quantities concerning the amplitude and latent period of the standard template by a value which is obtained by multiplying the characteristic quantities concerning the amplitude and latent period of the calibrational auditory P3 component with the correlation data between auditory sensation and visual sensation. FIG. 7(*b*) shows the waveform of an electroencephalogram signal which has been adjusted by the parameter for electroencephalogram signal adjustment calculated according to FIG. 7(*a*). It can be seen that the waveform of the electroencephalogram signal is adjusted in the adjustment zone of 200-500 ms. As used herein, the "waveform" refers to the amplitude of the electroencephalogram signal.

With such a construction, it becomes possible to present an auditory stimulation as a calibrational stimulation at the time of menu item presentation, and adjust the distinction method for a visual P3 component in the electroencephalogram interface by using a P3 component of an event-related potential responsive to the calibrational auditory stimulation. An electroencephalogram distinction is enabled which is based on the user's state immediately before use of an electroencephalogram interface, whereby the distinction ratio is improved.

Next, with reference to a flowchart of FIG. 8, an overall processing procedure which is performed by the electroencephalogram distinction method adjustment system 1 in FIG. 3 will be described.

Figure 8:
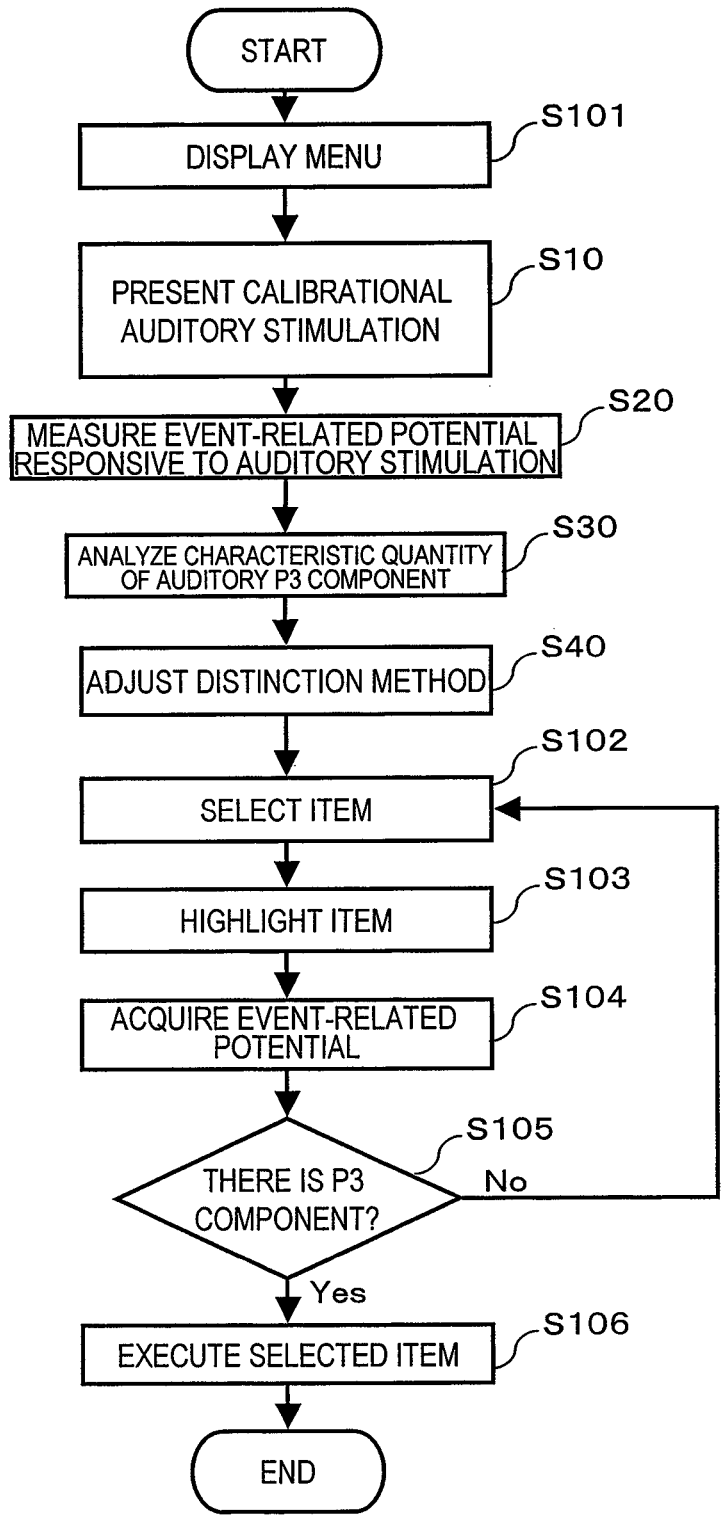
FIG. 8 A flowchart showing a procedure of processing where a calibration is performed in the electroencephalogram interface system 1 and thereafter an electroencephalogram interface is used.

FIG. 8 shows a procedure of processing where a calibration is performed in the electroencephalogram interface system 1, and thereafter an electroencephalogram interface is used. One feature of the processing procedure shown in FIG. 8 is that an auditory stimulation for calibration purposes is presented at the same time as the menu item presentation, and there is provided a step of adjusting the distinction method for the visual P3 component used in the electroencephalogram interface based on an auditory P3 component responsive to the auditory stimulation.

Note that, step S101 to step S106 shown in FIG. 8 are identical to the processing procedure by the electroencephalogram interface shown in FIG. 3. Therefore, descriptions thereof will be omitted below.

At step S10, the stimulation presentation section 11 presents an auditory stimulation for calibration purposes via the loudspeakers 3*b*. Although step S10 is performed next to step S101 in FIG. 8, the process of step S10 actually occurs at the same time that the electroencephalogram interface section 100 presents menu items on the screen 3*a*, whereby an auditory stimulation is presented.

At step S20, the biological signal measurement section 50 measures the event-related potential of the electroencephalogram of the user 5 for the duration of e.g. 500 ms since the point of presenting the auditory stimulation at step S10 as a starting point. Note that the biological signal measurement section 50 may be continuously measuring the event-related potential and the electroencephalogram analysis section 12 may cut out the event-related potential for the duration of 500 ms since the point of presenting the auditory stimulation as a starting point, whereby substantially the same data will be obtained.

At step S30, the electroencephalogram analysis section 12 analyzes the auditory P3 component of the event-related potential measured at step S20, and calculates the amplitude and latent period of the auditory P3 component as characteristic quantities. As for the calculation of the characteristic quantities, the event-related potential measured at step S20 may be subjected to a 2 Hz low-pass filter, for example. As a result, the influences of the electro-oculographic potential and the background electroencephalogram can be reduced.

At step S40, based on the characteristic quantities of the auditory P3 component analyzed at step S30 and on the modality conversion DB 13, the distinction method adjustment section 14 adjusts the parameter for the distinction of the visual P3 component. Since the modality conversion DB 13 defines a correlation between the auditory P3 component and the visual P3 component as mentioned above, a visual P3 component to be used for electroencephalogram distinction in the electroencephalogram interface section 100 can be obtained by referring to the modality conversion DB 13 by using the auditory P3 component as a key.

Regarding how the electroencephalogram distinction method is to be adjusted, as has been described with reference to FIG. 6 and FIG. 7, a template for distinguishing the visual P3 component that is stored in the electroencephalogram interface section 100 may be adjusted, or the waveform of the event-related potential measured by the biological signal measurement section 50 may be adjusted.

After the adjustment is completed, step S102 to step S106 are executed.

Next, with reference to the flowcharts from FIG. 9 to FIG. 11, the processes of step S30 and S40 will be described in detail.

Figure 9:
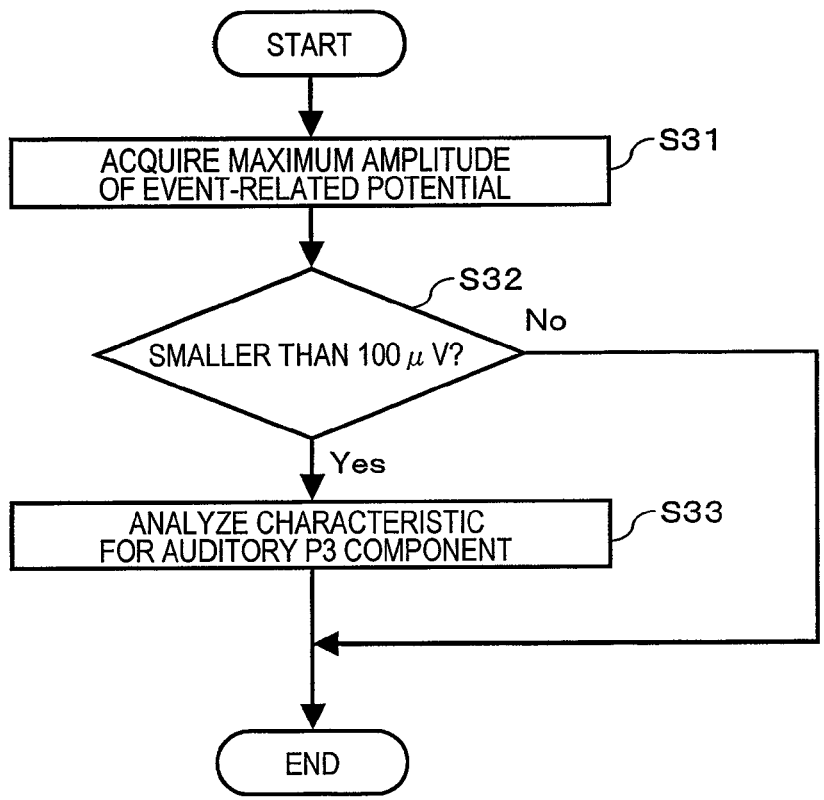
FIG. 9 A flowchart showing a procedure of processing by an electroencephalogram analysis section 12 performed at step S30 in FIG. 8.

FIG. 9 shows a detailed procedure of the process by the electroencephalogram analysis section 12 which is performed at step S30 in FIG. 8. The electroencephalogram analysis section 12 switches its process depending on whether a large noise is mixed in the event-related potential after presentation of the calibrational auditory stimulation or not.

Specifically, at step S31 in FIG. 9, the electroencephalogram analysis section 12 calculates a maximum value of the absolute value of the event-related potential measured by the biological signal measurement section 50. At next step S32, the electroencephalogram analysis section 12 determines whether or not the value calculated at step S31 is smaller than 100 µV, which is supposed to be a reference value concerning mixing of an electro-oculographic potential (EOG) noise. If it is smaller than 100 µV, the process proceeds to step S33; if it is greater, i.e., 100 µV or more, the process is ended. The reason why the process is ended is that the noise influence will presumably be very strong when the maximum value of the absolute value of the event-related potential is 100 μV or more. At step S33, the electroencephalogram analysis section 12 analyzes a characteristic quantity(s) of the event-related potential.

Figure 10:
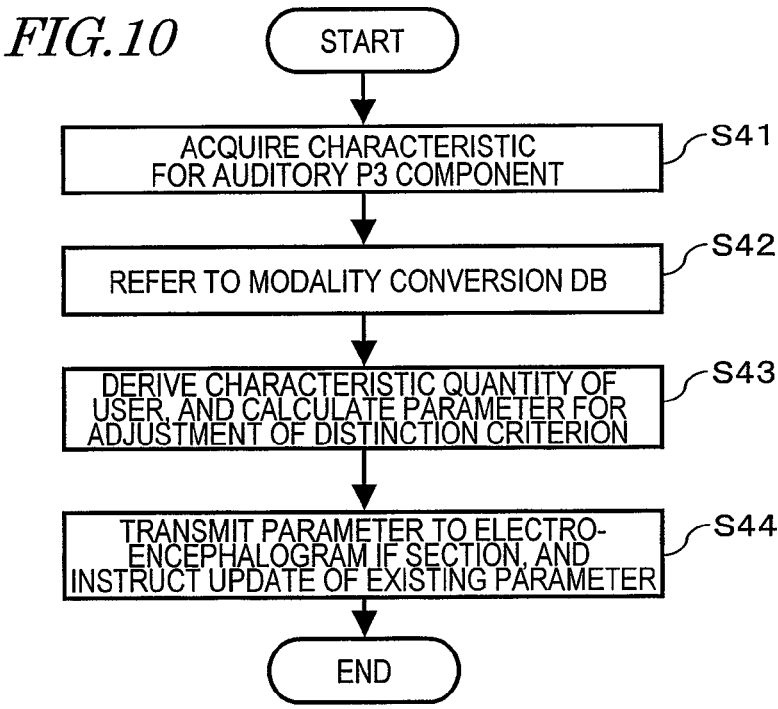
FIG. 10 A flowchart showing a procedure of processing by a distinction method adjustment section 14 performed at step S40 in FIG. 8.

Next, FIG. 10 shows a procedure of the process by the distinction method adjustment section 14 which is performed at step S40 in FIG. 8.

At step S41, the distinction method adjustment section 14 acquires amplitude and latent period as the characteristic quantities of the auditory P3 component calculated by the electroencephalogram analysis section 12. At step S42, as the correlation data between the auditory P3 component and the visual P3 component stored in the modality conversion DB 13, the distinction method adjustment section 14 refers to the information of amplitude, latent period, adjustment zone, for example.

At step S43, based on the information such as amplitude, latent period, adjustment zone acquired at step S41 and step S42, the characteristic quantities of that user are derived, and a parameter for adjustment of the distinction criterion is calculated. The calculation of the parameter can be achieved through multiplication, as has been described with reference to FIG. 6.

At step S44, the distinction method adjustment section 14 transmits the parameter for adjustment of the distinction criterion calculated at step S43 to the electroencephalogram interface section 100, and instructs it to update the existing parameter.

Figure 11:
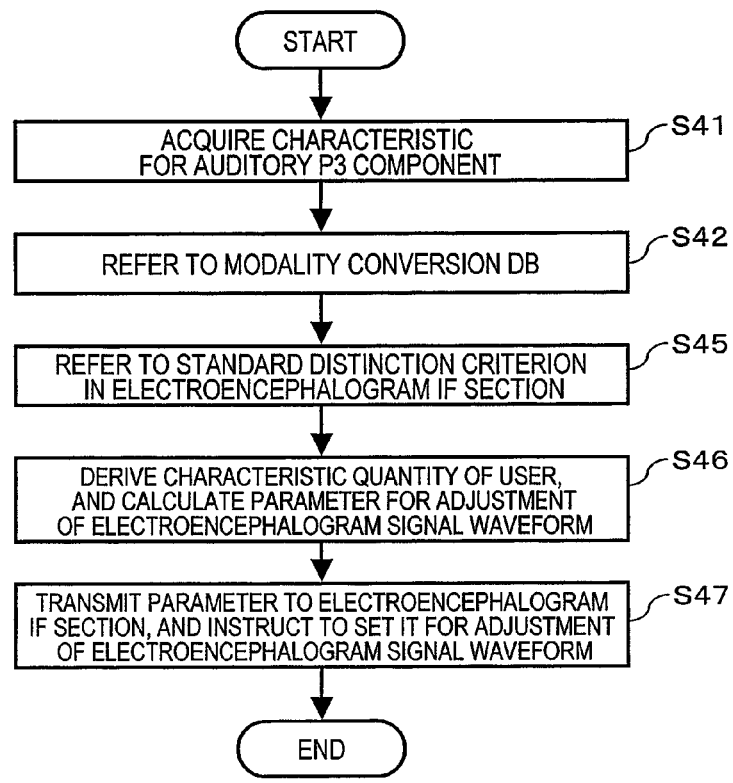
FIG. 11 A flowchart showing a procedure of a process of adjusting an electroencephalogram signal which is previously acquired in a biological signal measurement section 50.

Note that the distinction method shown in FIG. 11 may be used instead of the distinction method shown in FIG. 10. FIG. 11 shows a procedure of the process of adjusting an electroencephalogram signal which is previously acquired at the biological signal measurement section 50. In FIG. 11, any step where the same process as in FIG. 10 is denoted by the same reference numeral, and the description thereof is omitted.

At step S45, the distinction method adjustment section 14 refers to a standard distinction method that is stored in the electroencephalogram interface section 100, such as a template which has been generated from an arithmetic mean waveform of different users. Then, at step S46, the distinction method adjustment section 14 derives the characteristic quantities of the user in question based on the information such as amplitude, latent period, adjustment zone acquired at step S41, step S42, and step S45, and calculates a parameter for adjustment of the distinction criterion. The calculation of the parameter can be achieved through multiplication and division, as has been described with reference to FIG. 7.

At step S47, the distinction method adjustment section 14 transmits the parameter for electroencephalogram signal adjustment calculated at step S46 to the electroencephalogram interface section 100, and instructs the electroencephalogram interface section 100 to adjust the electroencephalogram signal based on that parameter.

Through the above process, the distinction method for a visual P3 component in the electroencephalogram interface is adjusted by using a P3 component of an event-related potential responsive to an auditory stimulation which is presented at the same time as the menu items, and a distinction which is in accordance with the user's state and the manner in which the electrodes are worn immediately before manipulating the electroencephalogram interface can be realized. As a result, the distinction ratio for a visual P3 component used in the electroencephalogram interface is improved.

By providing the distinction method adjustment apparatus 10 in the electroencephalogram interface system 1 of the present embodiment, it becomes possible to distinguish the visual P3 component which is in accordance with the user's state and the manner in which the electrodes are worn immediately before manipulating the electroencephalogram interface, using a characteristic quantity(s) of the P3 component responsive to a calibrational auditory stimulation which is presented at the same time as the menu items. Since the distinction ratio can be improved, an electroencephalogram interface which is easy to use can be realized.

Embodiment 2

In the electroencephalogram interface system 1 according to Embodiment 1, the stimulation presentation section 11 presents an auditory stimulation for calibration purposes at the same time that the electroencephalogram interface section 100 presents menu items. As a result, the distinction method can be adjusted in accordance with the user's state and the manner in which the electrodes are worn immediately before using the electroencephalogram interface.

However, as mentioned earlier, the event-related potential has a low S/N. Therefore, there is a possibility that a correct calibration cannot be performed if a large noise such as an electro-oculographic potential is mixed at the same time that the calibrational stimulation is presented.

In the electroencephalogram interface system of the present embodiment, a calibrational auditory stimulation is presented with random timing or predetermined timing, without being limited to immediately before use of an electroencephalogram interface. Then, by using a characteristic quantity(s) of the auditory P3 component, the distinction method for the visual P3 component in the electroencephalogram interface is adjusted by measuring the user's state and the manner in which the electrodes are worn, which may be incessantly changing. This makes it possible to provide an electroencephalogram interface system which maintains a high distinction ratio.

Figure 12:
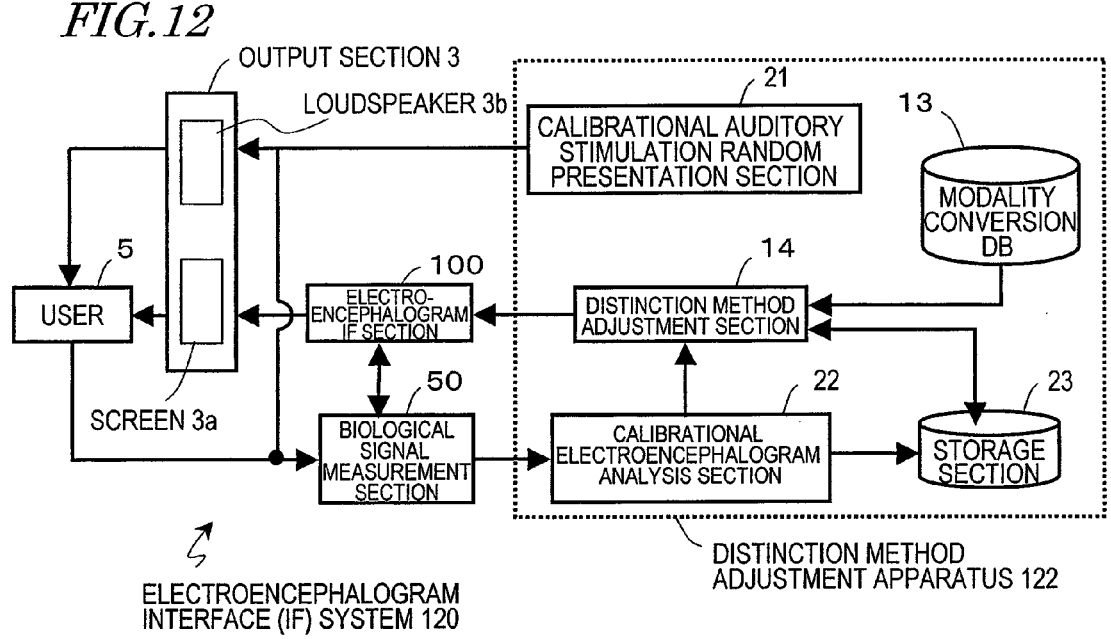
FIG. 12 A diagram showing a functional block construction of an electroencephalogram interface system 120 according to Embodiment 2.

FIG. 12 shows the functional block construction of an electroencephalogram interface system 120 according to the present embodiment. FIG. 12 also shows detailed functional blocks of the distinction method adjustment apparatus 122. The user 5 block is illustrated for convenience of explanation.

The electroencephalogram interface system 120 differs from the electroencephalogram interface system 1 (FIG. 4) with respect to the construction of the distinction method adjustment apparatus 122. More specifically, in the distinction method adjustment apparatus 122, a calibrational auditory stimulation random presentation section 21 and a calibrational electroencephalogram analysis section 22 having different functions from those of the stimulation presentation section 11 and the electroencephalogram analysis section 12 of the distinction method adjustment apparatus 10 (FIG. 4) are provided, and a storage section 23 is introduced.

Hereinafter, the calibrational stimulation random presentation section 21 and the calibrational electroencephalogram analysis section 22 will be described, which will be referred to as the "stimulation random presentation section 21" and the "electroencephalogram analysis section 22", respectively. Note that, among the component elements of the electroencephalogram interface system 120, component elements which are identical to those of the electroencephalogram interface system 1 (FIG. 4) will be denoted by like reference numerals, and the descriptions thereof will be omitted.

The stimulation random presentation section 21 presents to the user 5 an auditory stimulation for calibration purposes with random timing or predetermined timing. Random timing may be any frequency that does not overly bother a user who is viewing a program by using the TV 2, and may be arbitrary points in time at intervals of 20 minutes or more, for example. Predetermined timing may be based on an interval of about 10 minutes, for example, or an interval of 5 minutes, 20 minutes, or 1 hour. Note that the auditory stimulation may be the same as in the example described in Embodiment 1, e.g., a 1000 Hz toneburst or a device's operating sound. It does not matter whether there is one kind or a plurality of kinds.

Based on a starting point which is the timing of the stimulation random presentation section 21 presenting an auditory stimulation, the electroencephalogram analysis section 22 measures a characteristic quantity(s) of the event-related potential of the user 5 as measured by the biological signal measurement section 50.

The storage section 23 is a semiconductor memory or a hard disk, for example. From the electroencephalogram analysis section 22, the storage section 23 receives and stores the waveforms of the event-related potentials obtained from the most recent n times of calibration. As for the number of waveforms to be stored, the waveforms of the event-related potentials which are obtained responsive to the calibrational stimulations which have been presented during the 30 minutes before use of an electroencephalogram interface may be used. Without even providing the storage section 23, the waveforms of event-related potentials might be stored on a storage medium that stores the modality conversion DB 13.

The characteristic quantity(s) of the event-related potential to be analyzed by the electroencephalogram analysis section 22 is the same as in the case of the electroencephalogram analysis section 12 (FIG. 4). However, the method of analysis is different. In the electroencephalogram analysis section 22, it is determined as to whether a noise is contained in the event-related potential after presentation of the calibrational auditory stimulation or not. If no noise is contained, an arithmetic mean of the waveforms from the most recent n times among the event-related potentials stored in the storage section 23 is taken, and the amplitude and latent period of the auditory P3 component is calculated from the arithmetic mean waveform. The number n of additions may be five, for example, or may be the number of calibrational stimulations which have been presented during the 30 minutes before use of an electroencephalogram interface.

By adopting the above analysis method, it becomes possible to calculate the amplitude and latent period of the auditory P3 component more accurately, while reducing the influences of noise. This makes it possible to more accurately calculate the adjustment parameter of the distinction method in the distinction method adjustment section 14, whereby the distinction ratio for the visual P3 component in the electroencephalogram interface section 100 can be improved.

Next, with reference to the flowchart of FIG. 13, an overall procedure of processing that is performed by the electroencephalogram interface system 120 will be described.

Figure 13:
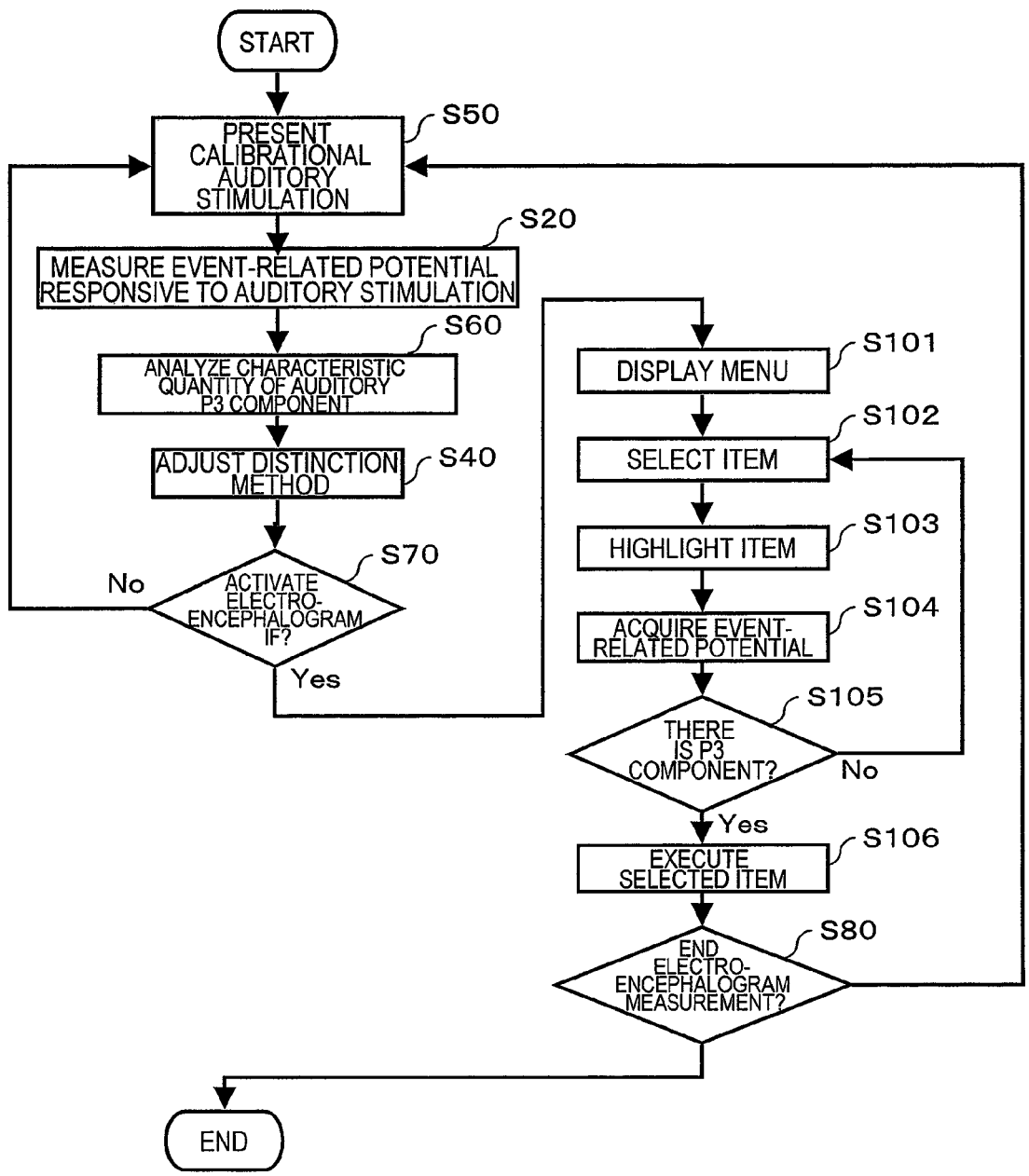
FIG. 13 A flowchart showing a processing procedure by the electroencephalogram interface system 120 according to Embodiment 2.

FIG. 13 shows a processing procedure by the electroencephalogram interface system 120 of the present embodiment. Any step where the same process as the process by the electroencephalogram interface system 1 (FIG. 8) is denoted by the same reference numeral, and the description thereof is omitted. Specifically, the processes of step S20, step S40, and step S101 to step S106 are common to the electroencephalogram interface systems 1 and 120.

At step S50, the stimulation random presentation section 21 presents an auditory stimulation for calibration purposes with random timing.

At step S60, the electroencephalogram analysis section 22 analyzes a characteristic quantity(s) of the event-related potential measured by the biological signal measurement section 50, from the timing of presenting an auditory stimulation at step S50 as a starting point. The detailed processes for the analysis will be described later.

At step S70, the electroencephalogram interface section 100 determines whether an electroencephalogram interface has been activated or not, e.g., a menu item has been displayed or not. If an electroencephalogram interface has been activated, the process proceeds to step S101; if an electroencephalogram interface has not been activated, the process returns to step S50. In the latter case, the stimulation random presentation section 21 continues the process of presenting auditory stimulations with random timing.

At step S80, the electroencephalogram interface section 100 determines whether electroencephalogram measurement has been finished or not. If the user 5 takes off the biological signal measurement section 50, which is an electroencephalograph, and electroencephalogram measurement is finished, the process is ended; if electroencephalogram measurement is to be continued, the process returns to step S50.

As described above, by providing the process of returning to step S50 of presenting an auditory stimulation for calibration purposes, it becomes possible to perform calibrations even after the user has begun using the electroencephalogram distinction method adjustment system 120. Therefore, even if the positions at which the electrodes of the biological signal measurement section 50 are worn are shifted to result in a different state of wearing or the arousal level of the user 5 is changed during use of the electroencephalogram distinction method adjustment system 120, it is possible to precisely recognize the event-related potential of an electroencephalogram signal.

Next, the detailed process of step S60 will be described with reference to the flowchart of FIG. 14.

Figure 14:
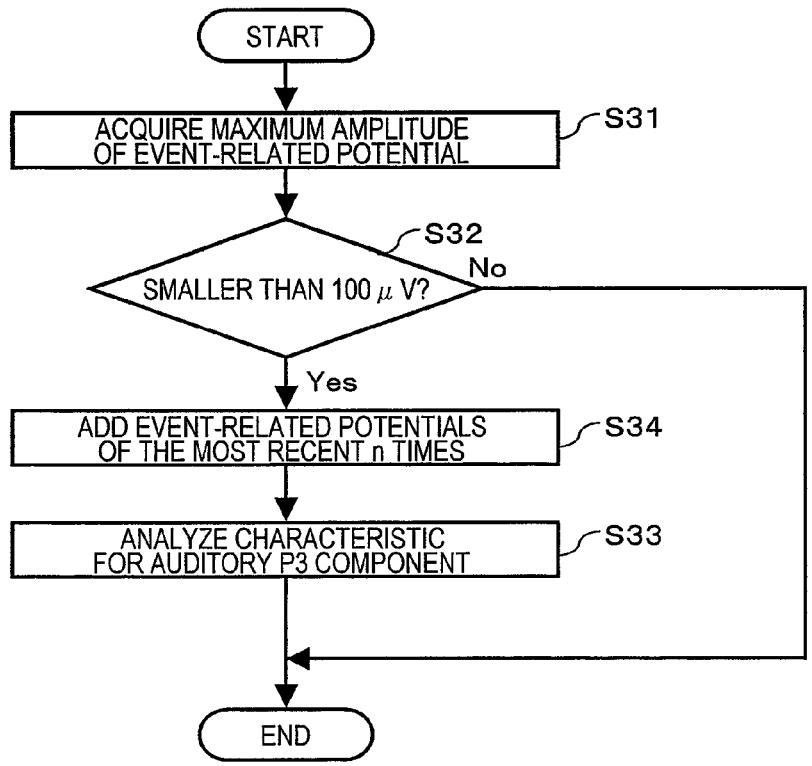
FIG. 14 A flowchart showing a procedure of processing by an electroencephalogram analysis section 22 performed at step S60 in FIG. 13.

FIG. 14 shows a procedure of processing by the electroencephalogram analysis section 22 performed at step S60 in FIG. 13. Note that any step where the same process as the process by the electroencephalogram interface system 1 shown in FIG. 9 is denoted by the same reference numerals, and the description thereof is omitted. Specifically, the processes of step S31, S32, and S33 are common to the electroencephalogram analysis sections 12 and 22.

At step S34, which is performed after step S32 and before step S33, the electroencephalogram analysis section 22 performs an addition of the event-related potentials of the most recent n times as measured by the biological signal measurement section 50 after presentation of the calibrational auditory stimulation. Through this addition, the influences of noise are reduced, and it becomes possible to calculate the amplitude and latent period of the auditory P3 component more accurately. As a result, a calibration which is immune to noises is realized. Note that the electroencephalogram analysis section 22 may perform an addition, rather than taking an arithmetic mean of the event-related potentials of the most recent n times.

By performing calibration by presenting auditory stimulations with random timing or predetermined timing, it becomes possible to adjust the distinction method for the visual P3 component of the event-related potential by precisely following the user's state and the manner in which the electrodes are worn, which may be incessantly changing. As a result, an improvement in the distinction ratio in the electroencephalogram interface can be realized.

Embodiment 3

The electroencephalogram interface systems of Embodiments 1 and 2 have been illustrated on the assumption that calibration is performed by using auditory stimulations such that the user will not overlook calibration stimulations.

However, an electroencephalogram interface system can be constructed so as to be directed not only to a stationary-type device as in the TV 2 shown in FIG. 1, but also to a portable-type device as an object of manipulation. When one takes a portable-type device outside and tries to manipulate it by using an electroencephalogram interface system, there is a possibility of missing the auditory stimulations which are presented in the middle of a crowd of people or on a train, for example. Moreover, there may be occasions where auditory stimulations should not be presented in terms of common courtesy. Therefore, there is a possibility that an appropriate calibration cannot be performed by presenting auditory stimulations.

As a calibrational stimulation, the electroencephalogram interface system 150 of the present embodiment presents a somatic stimulation, rather than an auditory stimulation. A somatic stimulation will entail a very low possibility of being overlooked by a user in a busy crowd. Therefore, even in the case where a calibration with an auditory stimulation is difficult, it is possible to adjust the distinction method for the visual P3 component in the electroencephalogram interface, whereby an improvement in the distinction ratio can be realized.

Figure 15:
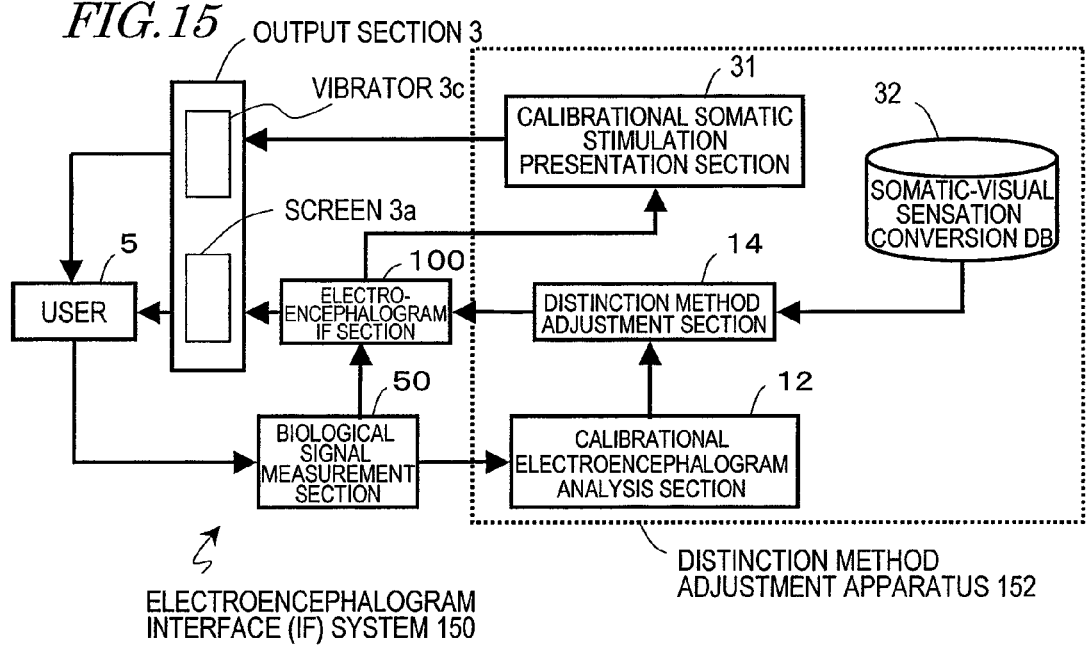
FIG. 15 A diagram showing a functional block construction of an electroencephalogram interface system 150 according to an embodiment.

FIG. 15 shows the functional block construction of the electroencephalogram interface system 150 according to the present embodiment. FIG. 15 also shows detailed functional blocks of the distinction method adjustment apparatus 152. The user 5 block is illustrated for convenience of explanation.

The electroencephalogram interface system 5 differs from the electroencephalogram interface system 1 (FIG. 4) in terms of the construction of the distinction method adjustment apparatus 152. More specifically, a calibrational somatic stimulation presentation section 31 and a somatic-visual sensation conversion database (DB) 32 are provided in the distinction method adjustment apparatus 152, which have different functions from those of the stimulation presentation section 11 and the modality conversion DB 13 of the distinction method adjustment apparatus 10 (FIG. 4). Note that FIG. 15 shows a vibrator 3c in the output section 3 of the electroencephalogram interface system 150; this is used for presenting a somatic stimulation (described later) to the user 5. Although no loudspeakers 3b (FIG. 4) are shown in the output section 3, this does not mean that loudspeakers 3b are to be excluded.

Hereinafter, the calibrational somatic stimulation presentation section 31 and the somatic-visual sensation conversion DB 32 will be described. In the following, they will be referred to as the "somatic stimulation presentation section 31" and the "conversion DB 32", respectively. Note that, among the component elements of the electroencephalogram interface system 150, component elements which are identical to those of the electroencephalogram interface system 1 (FIG. 4) will be denoted by like reference numerals, and the descriptions thereof are omitted.

At the same time as presenting menu items to the user 5 in the electroencephalogram interface section 100, the somatic stimulation presentation section 31 presents a somatic stimulation for calibration purposes via the vibrator 3c. The vibrator 3c operates upon receiving an instruction from the somatic stimulation presentation section 31 in a wireless or wired manner. Although it is contemplated that the vibrator 3c has a function of providing a vibration to the user while being worn on an arm of the user 5, as in the vibrator function of a mobile phone, this is only exemplary. Otherwise, a stimulation may simply be applied to the skin, e.g., a hand or the face. There may be one type of somatic stimulation, or two or more types of somatic stimulations.

The conversion DB 32 defines a correlation between the somatic P3 component and the visual P3 component.

The conversion DB 32 retains data for adjusting the distinction method for the visual P3 component in the electroencephalogram interface section 100 in accordance with the amplitude and latent period data of the P3 component with respect to an auditory stimulation as ascertained by the electroencephalogram analysis section 12, e.g., amplitude, latent period, and correction zone.

FIGS. 16(*a*) and (*b*) each show a data structure of the conversion DB 32. FIG. 16(*a*) shows a conversion DB 32 that defines conversion rules which are commonly applied to all users. On the other hand, FIG. 16(*b*) shows a conversion DB 32 that defines conversion rules which are switchably applied to different users by measuring a conversion criterion for each user in advance. As to how the P3 component of a visual event-related potential is obtained from an event-related potential responsive to a somatic stimulation by referring to the conversion DBs 32 of FIGS. 16(*a*) and (*b*), see the examples of FIGS. 5(*a*) and (*b*).

By incorporating the distinction method adjustment apparatus 152 including the aforementioned somatic stimulation presentation section 31 and conversion DB 32 into the electroencephalogram interface system 150, it becomes possible to adjust the distinction method based on the user's state and the manner in which the electrodes are worn by using a somatic stimulation, even in the case where a calibration with an auditory stimulation is not possible. As a result, the distinction ratio of the electroencephalogram interface section 100 can be improved.

Figure 17:
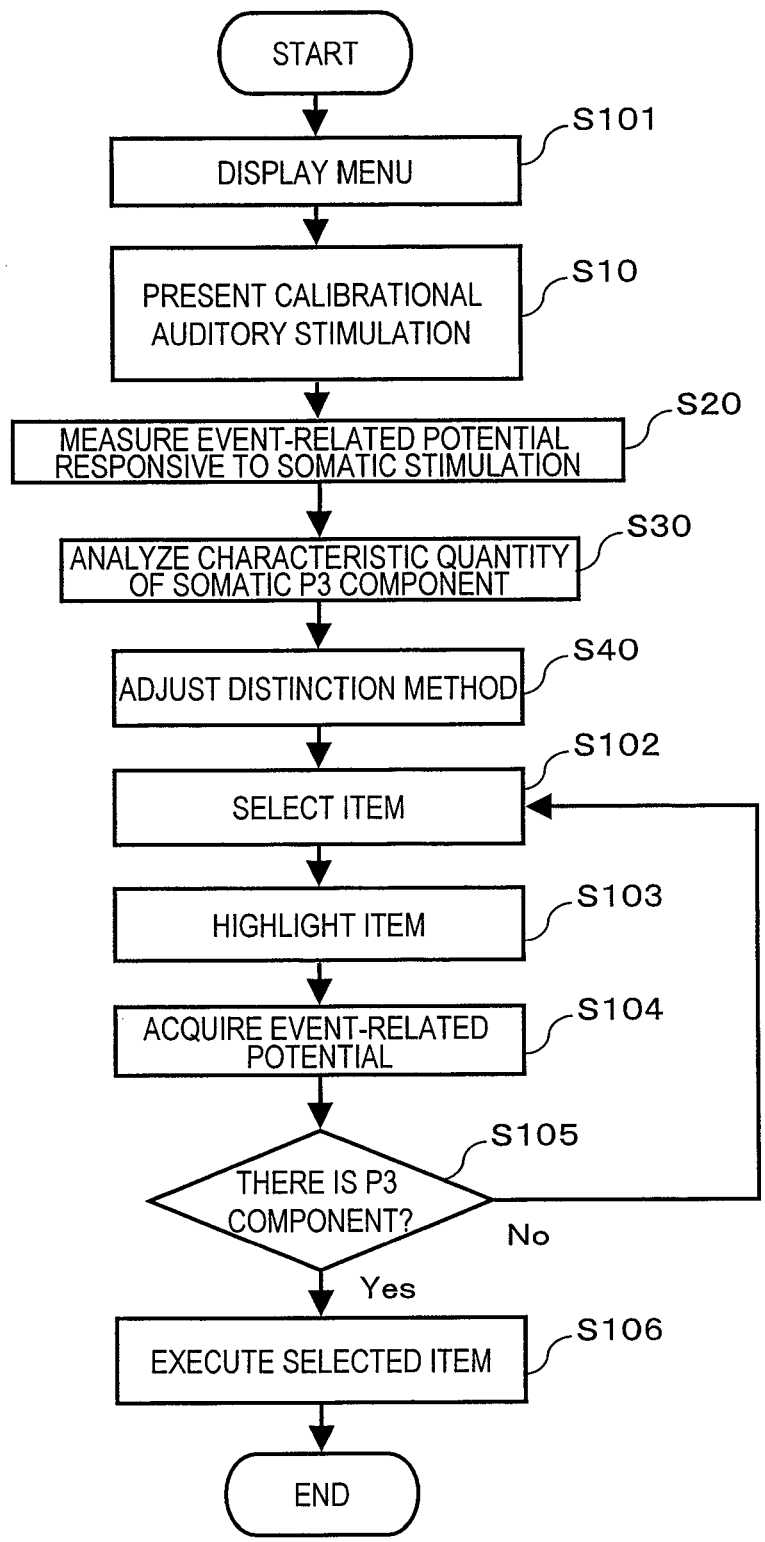
FIG. 17 A flowchart showing a processing procedure by the electroencephalogram interface system 150 according to Embodiment 3.

FIG. 17 shows a processing procedure by the electroencephalogram interface system 150 of the present embodiment. The flowchart of FIG. 17 is identical to the flowchart of FIG. 8 except that a somatic stimulation is used for calibration purposes and processing is performed by utilizing a somatic P3 component of an event-related potential based on that stimulation. Therefore, the description thereof is omitted, and the descriptions concerning FIG. 8 are relied upon.

According to the processing shown in FIG. 17, even in the case where a calibration with an auditory stimulation is not possible, the distinction method can be adjusted based on the user's state and the manner in which the electrodes are worn, by using a somatic stimulation. As a result, an improvement in the distinction ratio of an electroencephalogram interface can be realized.

Note that a calibration using a somatic stimulation may be performed even in a situation where a calibration with an auditory stimulation is possible. Alternatively, a calibration may be performed by using an auditory stimulation and a somatic stimulation in conjunction.

INDUSTRIAL APPLICABILITY

With the distinction method adjustment apparatus according to the present invention and an electroencephalogram interface system in which the distinction method adjustment apparatus is incorporated, a distinction method for the visual P3 component to be used for a distinction in the electroencephalogram interface system is adjusted. Therefore, the influences of an individual user's state such as physical condition and changes in the manner in which the electrodes for electroencephalogram detection are worn, which would present a problem in an interface that constantly measures an electroencephalogram, are eliminated, and thus a distinction ratio for the electroencephalogram is maintained. As a result, device operations that are not intended by the user, which are ascribable to incorrect distinctions of the electroencephalogram, are reduced, whereby an improved manipulability of the electroencephalogram interface is realized. Since such a function of the distinction method adjustment apparatus can be implemented by a computer program, for example, it can be easily implemented without a significant modification of the system.

The invention claimed is:

1. In an electroencephalogram interface system having
an output section configured to visually present a manipulation menu for a device and to present a non-visual stimulation to a modality other than the visual sense,
a biological signal measurement section configured to acquire an electroencephalogram signal from a user, and
an electroencephalogram interface section configured to distinguish, by using a prestored parameter of visual event-related potential, a P3 component of a visual event-related potential contained in an electroencephalogram signal after the manipulation menu is presented, and to operate the device based on the distinguished P3 component,
an electroencephalogram distinction method adjustment apparatus to be used for adjusting a distinction method in the electroencephalogram interface section, comprising:
a database defining a correlation between a P3 component of an event-related potential obtained from a stimulation to a modality other than the visual sense and a P3 component of a visual event-related potential;
a stimulation presentation section configured to present the non-visual stimulation via the output section;
an analysis section configured to analyze an event-related potential contained in the electroencephalogram signal after the non-visual stimulation is presented; and
a distinction method adjustment section configured to derive at least one of an amplitude and a latent period of a P3 component as a characteristic quantity of the user concerning the P3 component of a visual event-related potential based on a P3 component of the analyzed event-related potential from the non-visual stimulation and the correlation in the database, and to adjust the electroencephalogram distinction method in the electroencephalogram interface section based on the characteristic quantity.

2. The electroencephalogram distinction method adjustment apparatus of claim 1, wherein the stimulation presentation section presents an auditory stimulation as the non-visual stimulation.

3. The electroencephalogram distinction method adjustment apparatus of claim 1, wherein the stimulation presentation section presents a somatic stimulation as the non-visual stimulation.

4. The electroencephalogram distinction method adjustment apparatus of claim 1, wherein,
the electroencephalogram interface section distinguishes presence or absence of a P3 component of a visual event-related potential of the user based on a threshold value which is set as the parameter; and
the distinction method adjustment section adjusts the threshold value based on the characteristic quantity.

5. The electroencephalogram distinction method adjustment apparatus of claim 1, wherein,
the electroencephalogram interface section distinguishes presence or absence of a P3 component of a visual event-related potential of the user based on a template waveform of visual event-related potential which is set as the parameter; and
the distinction method adjustment section adjusts the template based on the characteristic quantity.

6. The electroencephalogram distinction method adjustment apparatus of claim 1, wherein the distinction method adjustment section adjusts an electroencephalogram signal of the user based on the characteristic quantity.

7. The electroencephalogram distinction method adjustment apparatus of claim 4, wherein,
the electroencephalogram interface section distinguishes presence or absence of a P3 component of the visual event-related potential based on a threshold value concerning amplitude of visual event-related potential;
the database defines a correlation concerning amplitude of the P3 component; and
the distinction method adjustment section adjusts the threshold value based on a characteristic quantity concerning amplitude.

8. The electroencephalogram distinction method adjustment apparatus of claim 5, wherein,
the database defines a correlation concerning amplitude of the P3 component; and
the distinction method adjustment section adjusts the template based on a characteristic quantity concerning amplitude.

9. The electroencephalogram distinction method adjustment apparatus of claim 6, wherein,
the database defines a correlation concerning amplitude of the P3 component; and
the distinction method adjustment section adjusts the electroencephalogram signal based on a characteristic quantity concerning amplitude.

10. The electroencephalogram distinction method adjustment apparatus of claim 1, wherein the stimulation presentation section presents a stimulation when use of the electroencephalogram interface system is begun.

11. The electroencephalogram distinction method adjustment apparatus of claim 1, wherein the stimulation presentation section presents the stimulation at a random point in time during a period in which the electroencephalogram interface system is being used.

12. In an electroencephalogram interface system having
an output section configured to visually present a manipulation menu for a device and to present a non-visual stimulation to a modality other than the visual sense,
a biological signal measurement section configured to acquire an electroencephalogram signal from a user, and
an electroencephalogram interface section configured to distinguish, by using a prestored parameter of visual event-related potential, a P3 component of a visual event-related potential contained in an electroencephalogram signal after the manipulation menu is presented, and to operate the device based on the distinguished P3 component,
a method to be used for adjusting a distinction method for an electroencephalogram in the electroencephalogram interface section, comprising the steps of:
providing a database defining a correlation between a P3 component of an event-related potential obtained from a stimulation to a modality other than the visual sense and a P3 component of a visual event-related potential;
presenting the non-visual stimulation via the output section;

analyzing an event-related potential contained in the electroencephalogram signal after the non-visual stimulation is presented;

deriving at least one of an amplitude and a latent period of a P3 component as a characteristic quantity of the user concerning the P3 component of a visual event-related potential based on a P3 component of the analyzed event-related potential from the non-visual stimulation and the correlation in the database; and adjusting the electroencephalogram distinction method in the electroencephalogram interface section based on the characteristic quantity.

13. In an electroencephalogram interface system having an output section configured to visually present a manipulation menu for a device and to present a non-visual stimulation to a modality other than the visual sense, a biological signal measurement section configured to acquire an electroencephalogram signal from a user, and an electroencephalogram interface section configured to distinguish, by using a prestored parameter for visual event-related potential, a P3 component of a visual event-related potential contained in an electroencephalogram signal after the manipulation menu is presented, and to operate the device based on the distinguished P3 component, an electroencephalogram distinction method adjustment apparatus to be used for adjusting a distinction method in the electroencephalogram interface section, comprising:

a stimulation presentation section configured to present the non-visual stimulation via the output section;

an analysis section configured to analyze an event-related potential contained in the electroencephalogram signal after the non-visual stimulation is presented; and a distinction method adjustment section configured to derive, based on a correlation stored in a database between a P3 component of an event-related potential obtained from a stimulation to a modality other than the visual sense and a P3 component of a visual event-related potential and on a P3 component of the analyzed event-related potential, at least one of an amplitude and a latent period of the P3 component as a characteristic quantity of the user concerning the P3 component of the visual event-related potential, and to adjust the electroencephalogram distinction method in the electroencephalogram interface section based on the characteristic quantity.

14. In an electroencephalogram interface system having an output section configured to visually present a manipulation menu for a device and to present a non-visual stimulation to a modality other than the visual sense, a biological signal measurement section configured to acquire an electroencephalogram signal from a user, and an electroencephalogram interface section configured to distinguish, by using a prestored parameter for visual event-related potential, a P3 component of a visual event-related potential contained in an electroencephalogram signal after the manipulation menu is presented, and to operate the device based on the distinguished P3 component, a method to be used for adjusting a distinction method for an electroencephalogram in the electroencephalogram interface section, comprising the steps of:

presenting a non-visual stimulation via the output section;

analyzing an event-related potential contained in the electroencephalogram signal after the non-visual stimulation is presented;

based on a correlation stored in a database between a P3 component of an event-related potential obtained from a stimulation to a modality other than the visual sense and a P3 component of a visual event-related potential and on a P3 component of the analyzed event-related potential, deriving at least one of an amplitude and a latent period of the P3 component as a characteristic quantity of the user concerning the P3 component of the visual event-related potential; and adjusting the electroencephalogram distinction method in the electroencephalogram interface section based on the characteristic quantity.

* * * * *